United States Patent
Tontz

(10) Patent No.: US 9,028,496 B2
(45) Date of Patent: May 12, 2015

(54) DEVICE FOR ESTABLISHING SUPPORTIVE FORCES IN THE BONY STRUCTURE OF A SKELETON

(76) Inventor: William L. Tontz, San Diego, CA (US)

(*) Notice: Subject to any disclaimer, the term of this patent is extended or adjusted under 35 U.S.C. 154(b) by 241 days.

(21) Appl. No.: 13/436,572

(22) Filed: Mar. 30, 2012

(65) Prior Publication Data

US 2013/0090655 A1 Apr. 11, 2013

Related U.S. Application Data

(60) Provisional application No. 61/474,721, filed on Apr. 12, 2011.

(51) Int. Cl.
| | | |
|---|---|---|
| A61B 17/56 | (2006.01) | |
| A61B 17/58 | (2006.01) | |
| A61F 2/30 | (2006.01) | |
| A61B 17/72 | (2006.01) | |
| A61B 17/74 | (2006.01) | |

(52) U.S. Cl.
CPC ......... *A61B 17/7233* (2013.01); *A61B 17/7275* (2013.01); *A61B 17/744* (2013.01)

(58) Field of Classification Search
USPC ........... 606/62–68, 99, 105; 623/17.11, 17.16
See application file for complete search history.

(56) References Cited

U.S. PATENT DOCUMENTS

| | | | |
|---|---|---|---|
| 5,176,681 A | 1/1993 | Lawes et al. | |
| 6,922,870 B2 | 8/2005 | Tontz, Sr. | |
| 2002/0165544 A1 | 11/2002 | Perren et al. | |
| 2003/0078581 A1 | 4/2003 | Frei et al. | |
| 2004/0133204 A1* | 7/2004 | Davies | 606/63 |
| 2005/0113836 A1* | 5/2005 | Lozier et al. | 606/80 |
| 2006/0064094 A1 | 3/2006 | Levy et al. | |
| 2006/0084998 A1* | 4/2006 | Levy et al. | 606/63 |
| 2007/0100342 A1* | 5/2007 | Green et al. | 606/64 |
| 2009/0005782 A1* | 1/2009 | Chirico et al. | 606/63 |

FOREIGN PATENT DOCUMENTS

EP 2298201 A1 3/2011

* cited by examiner

*Primary Examiner* — Mary Hoffman
*Assistant Examiner* — Michelle C Eckman
(74) *Attorney, Agent, or Firm* — Nydegger & Associates

(57) ABSTRACT

A device is provided for insertion into a human bone to replicate the biomechanical forces found in a healthy bone in a human skeleton. The device can be configured in several different ways and is customizable to meet the requirements of a particular bone. The device is constructed with a central shaft having a compression plate at one end and a base member at the other. A plurality of wires interconnects the compression plate and the base member. The central shaft is threaded at both ends, with one end threaded into the base member and the other end threaded into the compression plate. An actuator is used to urge the base member in the direction of the compression plate. This action forces the plurality of wires to bow in an outward direction to stabilize the device against the bony surface on the interior surface of a bone.

18 Claims, 3 Drawing Sheets

DEVICE FOR ESTABLISHING SUPPORTIVE FORCES IN THE BONY STRUCTURE OF A SKELETON

This application claims the benefit of U.S. Provisional Patent Application Ser. No. 61/474,721, filed Apr. 12, 2011.

FIELD OF THE INVENTION

The present invention pertains generally to devices that provide support for a bone of a human skeleton. More specifically, the present invention pertains to devices that provide internal support to unhealthy bones in a human skeleton. The present invention is particularly, but not exclusively, useful as a customizable, implantable device for replicating biomechanical forces normally present inside a healthy bone of a human skeleton.

BACKGROUND OF THE INVENTION

The bones of the human skeleton serve many important structural and mechanical purposes. Among them, the bones protect organs, provide a frame to support the body, and function along with muscle and tissue to allow parts of the body to move. During these and other tasks, the bones are subjected to various forces. In particular, the bones that serve as joints in the human body, like the knee or shoulder, are subjected to increased forces during movement of various body parts. To counteract these forces, bones use biomechanical forces to remain functional. In a healthy bone, these biomechanical forces help protect the healthy bone by counteracting forces that may be randomly applied on the bone. Through the use of a radiological device, an illustration of stress lines can be developed to show the types of forces a healthy bone needs to counteract. These forces will vary based on the unique characteristics of each bone in the human skeleton.

Numerous reasons can cause a bone in the human body to be weakened and require support. Support for a weakened bone can be provided either externally (i.e. outside the body), or internally, (i.e. in direct contact with a bone). In the case of external support, a splint or a cast can be placed on the skin over the weakened bone, such as a fractured femur, to provide short-term support. Regarding the case of internal support, various screws, rods, and pins can be affixed directly to the bone and are suitable for long-term support. In any of these cases, the support is directed towards allowing the bone to heal. And, in many cases, the internal or external support limits the movement or motion of the body part being supported. Furthermore, the internal or external support does not accurately replicate the biomechanical forces present in a healthy bone.

In light of the above, it is an object of the present invention to provide a device that can be implanted into a bone to replicate the biomechanical forces that are normally present in a healthy bone. Another object of the present invention is to provide a device that can be customized for a particular bone to replicate the unique biomechanical forces that are typically imposed on the bone in the human skeleton. Yet another object of the present invention is to provide a device that can be used for establishing supportive forces in the bony structure of a skeleton that is easy to use, is relatively simple to manufacture, and is comparatively cost effective.

SUMMARY OF THE INVENTION

In accordance with the present invention, a device is provided that can be implanted inside an unhealthy bone of a skeleton to provide internal support for the bone. To accomplish this, various configurations of a wire assembly can be constructed. In detail, depending on the anatomy of a particular bone, a single wire assembly, a secondary wire assembly, a bipartite wire assembly, or a compound wire assembly may be chosen for insertion into the bone. The particular assembly which is chosen is dependent on the anatomy of the bone in which the assembly is implanted and the biomechanical forces which need to be replicated to provide support to the selected bone.

Structurally, a single wire assembly in accordance with the present invention includes a base member that defines an axis. A compression plate that is centered on the axis, and is positioned at a distance "d" from the base member, is included as part of the assembly. Interconnecting the compression plate with the base member is a plurality of titanium wires. In detail, each wire in the plurality is individually coplanar with the axis, and each wire is distanced laterally from the axis, with each wire being the same lateral distance away from the axis. A central shaft is aligned along the axis and it interconnects the compression plate with the base member.

Also included in a single wire assembly is an actuator. Functionally, this actuator is used for acting on the central shaft to change the distance "d" between the compression plate and the base member. This change in the distance "d" is made through an increment "Δd", and it results in the movement of the plurality of wires between a first configuration and a second configuration. Specifically, in the first configuration, the wires are substantially parallel to each other. Thus, in this first configuration, the single wire assembly is substantially cylindrically shaped. In the second configuration, however, the wires are compressed and are deployed to extend laterally outward from the axis in a bowed configuration.

In the operation of a single wire assembly, the assembly is first inserted into the bone while it is in its first configuration. The actuator is then manipulated to change the single wire assembly from its first configuration into its second configuration. This is done to establish a rigid interaction between the deployed wires and the bony structure of the bone into which the assembly has been inserted. It is in this second configuration that the single wire assembly provides the supportive forces for the skeleton.

Depending on how the single wire assembly is to be used, it can either be a primary type assembly, or a secondary type assembly. The essential difference between the two types of assemblies is the structural cooperation between the actuator and the central shaft. For a primary type assembly, the central shaft will have a threaded first end, and it will have a second end that is mounted for rotation on the base member. In this case, the compression plate is formed with a threaded hole to receive the threaded first end of the central shaft. A bolt head that is affixed to the second end of the central shaft can then be manually rotated. This rotation will then change the distance "d" between the base member and the compression plate, to thereby move the primary type assembly from its first configuration into its second configuration.

For the secondary type assembly, the central shaft still has a threaded first end, but the second end is fixedly mounted on the base member. In this case, the compression plate is formed with a hole, and the actuator is a nut that is threaded onto the first end of the central shaft to urge the compression plate toward the base member. Rotation of this nut then moves the compression plate toward the base member to change the distance "d" between the compression plate and the base member. This then moves the secondary type assembly from the first configuration to the second configuration.

As implied above, it is to be appreciated that various combinations of primary type and secondary type wire assemblies can be made to form the different embodiments of the present invention. One such embodiment is a bipartite wire assembly that includes both a primary type assembly and a secondary type assembly. For the bipartite wire assembly, a primary type assembly and a secondary type assembly are coaxially aligned with each other. Also, they have a common base member.

In a variation of the bipartite wire assembly, the common base member has at least one end that is formed with a step. Specifically, this stepped end will have a first surface that is located at a distance "$d_1$" from the compression plate, and it will have a second surface that is located at a distance "$d_2$" from the compression plate. A first plurality of wires will then interconnect the first surface of the step with the compression plate and a second plurality of wires will interconnect the second surface of the step with the compression plate.

In another embodiment of the present invention a compound wire assembly includes a bipartite wire assembly and a primary type assembly. The interaction between these assemblies requires that the base member of the primary assembly be an elongated hollow cylinder that is formed with a longitudinal lumen. Additionally, the base member of this embodiment will be formed with a transverse hole that crosses the lumen at an angle "$\phi$". Specifically, this transverse hole receives the bipartite wire assembly to position the common base member of the bipartite wire assembly across the lumen of the base member. This embodiment also includes a screw that is inserted into the lumen of the base member to urge against the common base member of the bipartite wire, assembly. Thus, pressure from the screw holds the bipartite wire assembly on the primary type assembly for establishment of the compound wire assembly.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figures 1A, 1B:
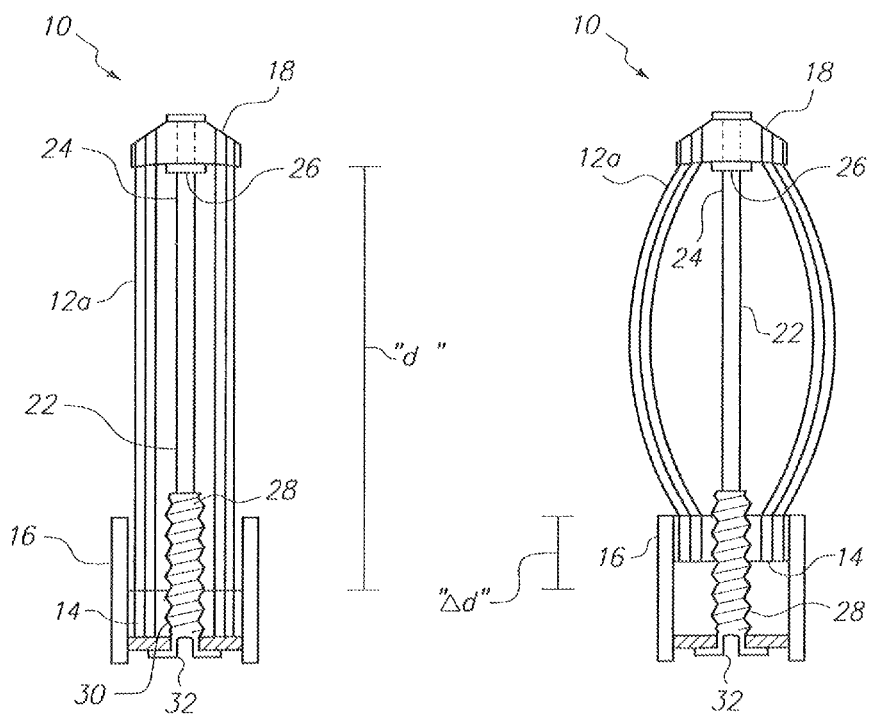
FIG. 1A is an elevation view of a single wire assembly in a configuration before being deployed.
FIG. 1B is a view of the single wire assembly shown in FIG. 1A after being reconfigured into a deployed configuration.

Referring initially to FIG. 1A, a primary type assembly is shown and is designated 10. As shown, the primary type assembly 10 is in a first configuration with a plurality of wires 12 (of which wire 12a is labeled and is exemplary) oriented substantially parallel to one another. It can be seen that the plurality of wires 12 extend between a base member 14 enclosed by an outer sleeve 16 and a compression plate 18 at a distance "d". An additional essential structural component is a central shaft 22 that interconnects the base member 14 and the compression plate 18. In detail, the central shaft 22 has a first end 24 that is received into a threaded opening 26 in the compression plate 18. And, the central shaft 22 is also constructed with a second end 28 that is also threaded and extends into a threaded opening 30 constructed in the center of the base member 14. At its second end 28, the central shaft 22 is formed with an actuator 32 that will be used to manipulate the primary type assembly 10 between the first configuration and the second configuration.

When viewed in conjunction with FIG. 1A, FIG. 1B can be used to describe the movement of the primary type assembly 10 from its first configuration (FIG. 1A) to its second configuration (FIG. 1B). The initial step is to insert the assembly 10 into a bone, while the primary type assembly 10 is in its first configuration. Once the primary type assembly 10 has reached a predetermined location in the bone, the actuator 32 is engaged to urge the base member 14 towards the compression plate 18. When the actuator 32 is engaged, the base member 14 moves a distance "$\Delta d$". During the movement of the base member 14 towards the compression plate 18, the plurality of wires 12 bow outward as shown in FIG. 1B. The wires 12 continue to bow outward until contact is established between the solid, bony surface of the inside of the bone into which the primary type assembly 10 has been inserted. In contacting the bony surface, the primary type assembly 10 is positioned securely against the bone and is able to closely replicate the supportive forces present if the bone was healthy.

Figure 2A:
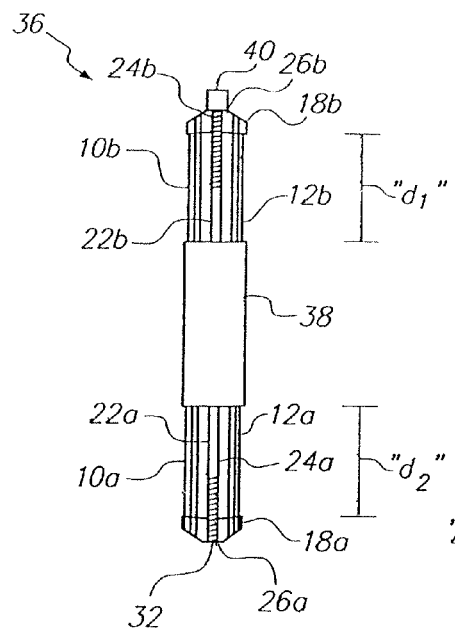
FIG. 2A is an elevation view of a bipartite wire assembly in a configuration before being deployed.

Now referring to FIG. 2A, a bipartite assembly 36 is shown in a first configuration. It can be seen that the bipartite assembly 36 is constructed with two coaxial assemblies 10a, b connected by a common base member 38. Assembly 10a is a primary type assembly, as depicted in FIGS. 1A and 1B, having a central shaft 22a, first end 24a, a threaded opening 26a, and an actuator 32 as described above. In this case, assembly 10b is a secondary type assembly that differs slightly from assembly 10a. Like the primary type assembly 10a, assembly 10b is formed with a central shaft 22b with a threaded first end, 24b that passes through a threaded opening 26b in the compression plate 18b. Unlike the primary type assembly 10a, a nut 40 is formed on the central shaft 22b to serve as the mechanism for moving the secondary type assembly 10b between the first and second configuration. In other words, the nut 40 replaces the actuator 32 that is used with a primary assembly 10. As shown, the distance between compression plate 18b and the common base member 38 is "$d_1$." And, the distance between compression plate 18a and the common base member 38 is "$d_2$."

Figure 2B:
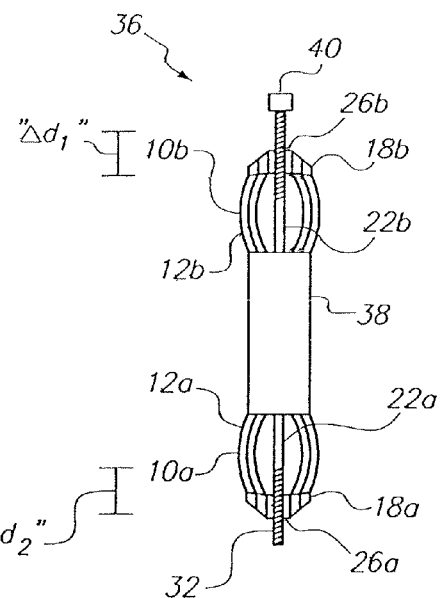
FIG. 2B is a view of the bipartite wire assembly shown in FIG. 2A after being reconfigured into a deployed configuration.

Referring to FIG. 2B, a bipartite wire assembly 36 is shown in its second configuration. Here, the actuator 32 of assembly 10a and the nut 40 of assembly 10b have both been engaged. As such, each assembly 10a, b moves from the first configuration to the second configuration. In detail, the actuator 32 moves the compression plate 18a of assembly 10a towards the common base member 38. Also, upon engagement of the nut 40, compression plate 18b of assembly 10b is moved towards the common base member 38. It can be seen that the wires (of which 12a, 12b are exemplary) on both assembly 10a and assembly 10b are both bowed outward in the second configuration of the bipartite wire assembly 36. As shown, the distance that compression plate 18a moves is $\Delta d_1$, and the distance compression plate 18b moves is $\Delta d_2$. The values for $\Delta d_1$ and $\Delta d_2$ do not have to be equal and will be based on the structure of the individual bone into which the bipartite wire assembly 36 has been inserted.

Figure 3:
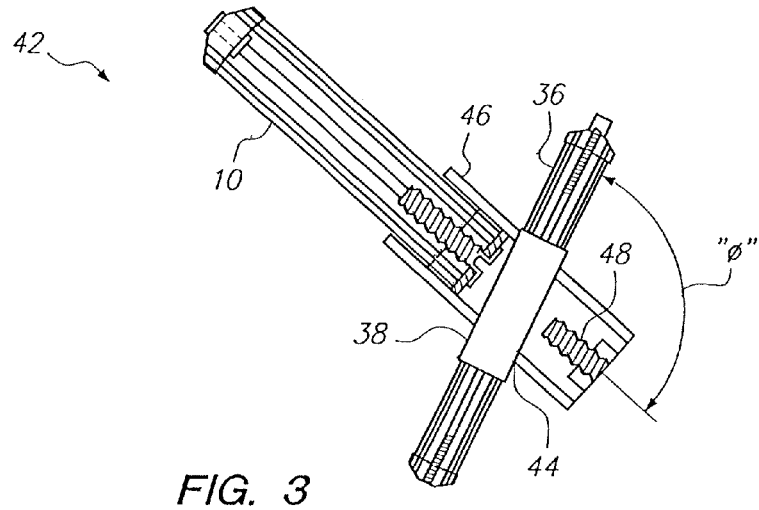
FIG. 3 is a view of a compound wire assembly in a configuration before being deployed.

In FIG. 3, a compound wire assembly 42 is shown in a first configuration before being deployed into a bone. As shown, the compound wire assembly 42 is formed by inserting a bipartite wire assembly 36 into a transverse hole 44 formed on an elongated base member 46 of a primary type assembly 10. This transverse hole 44 crosses the elongated base member 46 at an angle "φ," which is determined by the orientation required for the use of the bipartite assembly 36 after insertion into a particular bone. An additional feature of the elongated base member 46 used with the compound wire assembly 42 is a stabilizing screw 48. When tightened, the stabilizing screw 48 contacts the outer surface of the common base member 38 to stabilize the joining of the primary type assembly 10 and the bipartite wire assembly 36. In all other aspects, the individual assemblies that make up the compound wire assembly 42 are substantially the same as disclosed previously.

Figure 4:
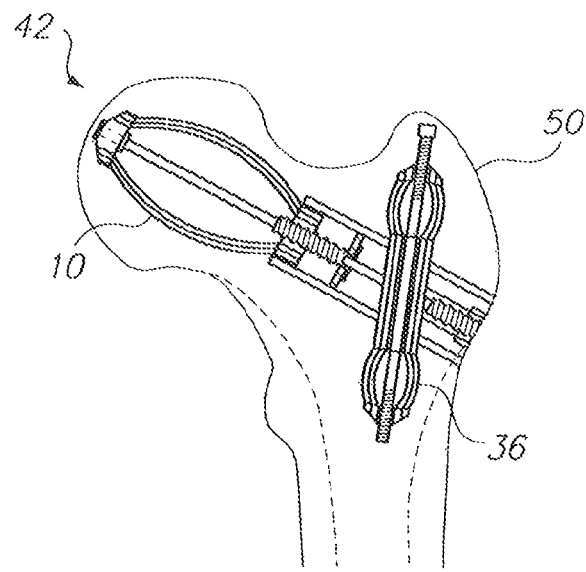
FIG. 4 is a cross section view of a femur, shown with a compound wire assembly of FIG. 3 deployed to replicate biomechanical stresses in the femur head.

Referring now to FIG. 4, a compound wire assembly 42 is shown in an operational environment in a femur 50. It can be seen that the compound wire assembly 42 is in its second configuration with the wires of the primary type assembly 10 and the bipartite wire assembly 36 bulging outward to make contact with the interior surface of the bone.

Figure 5:
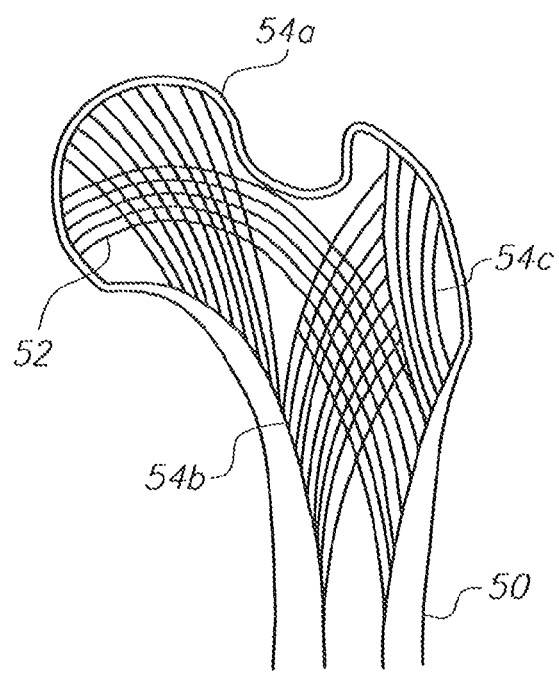
FIG. 5 is a schematic view of Singh lines in a femur.

Finally, referring to FIG. 5, Singh lines in a femur 50 are shown. Stated simply, Singh lines are radiologically evaluated stress lines in a bone. These lines indicate the tensile forces 52 and compressive forces 54a, 54b, 54ca bone must withstand. Consequently, these tensile forces 52 and compressive forces 54a-c are the same forces the device of the present invention will counteract when inserted into a bone. Prior to the selection of a specific assembly, the Singh lines of a bone will be modeled and analyzed. Once the Singh lines have been modeled and analyzed, a particular assembly (primary, secondary, bipartite, compound) can be selected and customized to replicate the tensile forces 52 and compressive forces 54a-c indicated by the Singh lines.

While the particular Device for Establishing Supportive Forces in the Bony Structure of a Skeleton as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for establishing supportive forces inside a bony structure of a skeleton, wherein the device comprises:
   a first base member defining a first axis;
   a first compression plate centered on the first axis and positioned at a distance "$d_1$" from the first base member;
   a first plurality of wires interconnecting the first compression plate with the first base member, wherein each wire is individually coplanar with the first axis and is distanced laterally therefrom;
   a first central shaft aligned along the first axis to interconnect the first compression plate with the first base member, the first central shaft formed with a transverse hole;
   a first actuator for acting on the first central shaft to change the distance "$d_1$" between the first compression plate and the first base member by an increment "$\Delta d_1$", to move the first plurality of wires between a first configuration wherein the wires are substantially parallel to each other, and a second configuration wherein the wires are compressed and deployed to extend laterally outward from the first axis in a bowed configuration;
   a second base member defining a second axis, the second base member received within the transverse hole formed in the first central shaft;
   a second compression plate centered on the second axis and positioned at a distance "$d_2$" from the second base member;
   a second plurality of wires interconnecting the second compression plate with the second base member, wherein each wire is individually coplanar with the second axis and is distanced laterally therefrom;
   a second central shaft aligned along the second axis to interconnect the second compression plate with the second base member, the second central shaft formed with a transverse hole; and
   a second actuator for acting on the second central shaft to change the distance "$d_2$" between the second compression plate and the second base member by an increment "$\Delta d_2$", to move the second plurality of wires between a first configuration wherein the wires are substantially parallel to each other, and a second configuration wherein the wires are compressed and deployed to extend laterally outward from the second axis in a bowed configuration to provide supportive forces for the skeleton when the device is embedded in a bone of the skeleton.

2. A device as recited in claim 1 wherein the first central shaft has a threaded first end and a second end mounted for rotation on the first base member, wherein the first compression plate is formed with a threaded hole for receiving the threaded first end of the first central shaft, and further wherein the first actuator is a bolt head affixed to the second end of the first central shaft for moving the first plurality of wires from the first configuration to the second configuration in response to a rotation of the first actuator.

3. A device as recited in claim 1 wherein the first central shaft has a threaded first end and a second end fixedly mounted on the first base member, wherein the first compression plate is formed with a hole, and further wherein the first actuator is a nut mounted onto the first end of the first central shaft for moving the first plurality of wires from the first configuration to the second configuration in response to a rotation of the first actuator.

4. A device as recited in claim 3 wherein the second base member is a common base member and the device further comprises a third compression plate centered on the second axis and positioned at a distance "$d_3$" from the common base member, and with a third plurality of wires interconnecting the third compression plate with the common base member, wherein each wire in the third plurality of wires is individually coplanar with the second axis and is distanced laterally therefrom, and further wherein the second central shaft interconnects the third compression plate with the common base member, and with the second actuator for acting on the second central shaft to change the distance "$d_3$" between the third compression plate and the common base member by an increment "$\Delta d_3$", to move the third plurality of wires between a first configuration wherein the wires are substantially parallel to each other, and a second configuration wherein the wires are compressed and deployed to extend laterally outward from the second axis in a bowed configuration.

5. A device as recited in claim 4 wherein the device further comprises a screw inserted into a lumen formed in the first base member for a threaded engagement therewith to urge the screw against the common base member to hold the first base member on the common base member for establishment of a compound assembly.

6. A device as recited in claim 5 wherein the transverse hole crosses the lumen of the first base member at an angle "φ".

7. A device as recited in claim 1 wherein each wire in the first plurality of wires is made of titanium.

8. A device as recited in claim 1 wherein the second configuration is characterized by a rigid interaction between the deployed wires and the bony structure of the skeleton.

9. A device for establishing supportive forces inside a bony structure of a skeleton which comprises:
   a first assembly having a first base member defining a first axis, with a first compression plate centered on the first axis and positioned at a first distance "$d_1$" from the first base member, and with a first plurality of wires interconnecting the first compression plate with the first base member, wherein each wire is individually coplanar with the first axis and is distanced laterally therefrom, and further with a first central shaft aligned along the first axis and formed with a transverse hole to interconnect the first compression plate with the first base member;
   a second assembly having a second base member defining a second axis, with a second compression plate centered on the second axis and positioned at a distance "$d_2$" from the second base member, and with a second plurality of wires interconnecting the second compression plate with the second base member, wherein each wire is individually coplanar with the second axis and is distanced laterally therefrom, and further with a second central shaft aligned along the second axis to interconnect the second compression plate with the second base member, and wherein the second assembly is received within the transverse hole in the first central shaft;
   a first actuator connected to the first central shaft for acting on the first central shaft to change the distance "$d_1$" between the first compression plate and the first base member by an increment "$\Delta d_1$", to move the first plurality of wires between a first configuration wherein the wires are substantially parallel to each other, and a second configuration wherein the wires are compressed and deployed to extend laterally outward from the first axis to provide supportive forces for the skeleton when the device is embedded in a bone of the skeleton; and
   a second actuator connected to the second central shaft for acting on the second central shaft to change the distance "$d_2$" between the second compression plate and the second base member by an increment "$\Delta d_2$", to move the second plurality of wires between a first configuration wherein the wires are substantially parallel to each other, and a second configuration wherein the wires are compressed and deployed to extend laterally outward from the second axis to provide supportive forces for the skeleton when the device is embedded in a bone of the skeleton.

10. A device as recited in claim 9 wherein the first central shaft has a threaded first end and a second end mounted for rotation on the first base member, wherein the first compression plate is formed with a threaded hole for receiving the threaded first end of the first central shaft, and further wherein the first actuator is a bolt head affixed to the second end of the first central shaft for moving the first plurality of wires from the first configuration to the second configuration in response to a rotation of the first actuator.

11. A device as recited in claim 9 wherein the first central shaft has a threaded first end and a second end fixedly mounted on the first base member, wherein the first compression plate is formed with a hole, and further wherein the first actuator is a nut mounted onto the first end of the first central shaft for moving the first plurality of wires from the first configuration to the second configuration in response to a rotation of the first actuator.

12. A device as recited in claim 11 wherein the second base member is a common base member and the device further comprises a third compression plate centered on the second axis and positioned at a distance "$d_3$" from the common base member, and with a third plurality of wires interconnecting the third compression plate with the common base member, wherein each wire in the third plurality of wires is individually coplanar with the second axis and is distanced laterally therefrom, and further with the second central shaft interconnecting the third compression plate with the common base member and a third actuator for acting on the second central shaft to change the distance "$d_3$" between the third compression plate and the common base member by an increment "$\Delta d_3$", to move the third plurality of wires between a first configuration wherein the wires are substantially parallel to each other, and a second configuration wherein the wires are compressed and deployed to extend laterally outward from the second axis in a bowed configuration.

13. A device as recited in claim 12 wherein the device further comprises a screw inserted into a lumen formed in the first base member for a threaded engagement therewith to urge the screw against the common base member to hold the first base member on the common base member for establishment of a compound assembly.

14. A method for establishing supportive forces inside a bony structure of a skeleton which comprises the steps of:
   providing a first assembly having a first base member defining a first axis, with a first compression plate centered on the first axis and positioned at a first distance "$d_1$" from the first base member, and with a first plurality of wires interconnecting the first compression plate with the first base member, wherein each wire is individually coplanar with the first axis and is distanced laterally therefrom, and further with a first central shaft aligned along the first axis to interconnect the first compression plate with the first base member, and wherein an elongated base member extends from the first base member and is formed with a transverse hole;
   positioning a second assembly within the transverse hole of the first elongated base member, the second assembly having a second base member defining a second axis, with a second compression plate centered on the second axis and positioned at a distance "$d_2$" from the second base member, and with a second plurality of wires interconnecting the second compression plate with the second base member, wherein each wire is individually coplanar with the second axis and is distanced laterally therefrom, and further with a second central shaft aligned along the second axis to interconnect the second compression plate with the second base member;
   acting on the first central shaft to change the distance "$d_1$" between the first compression plate and the first base member by an increment "$\Delta d_1$" and acting on the second central shaft to change the distance "$d_2$" between the second compression plate and the second base member by an increment "$\Delta d_2$", to move the first and second plurality of wires from a first configuration wherein the wires are substantially parallel to each other, and into a second configuration wherein the wires are compressed and deployed to extend laterally outward from the respective axis in a bowed configuration to provide supportive forces for the skeleton when the device is embedded in a bone of the skeleton.

15. A method as recited in claim 14 further comprising the step of embedding the first and second assemblies in the first configuration into the bone of the skeleton.

16. A method as recited in claim 15 wherein the first central shaft has a threaded first end and a second end mounted for rotation on the first base member, wherein the first compression plate is formed with a threaded hole for receiving the threaded first end of the first central shaft, and further wherein the step of acting on the first central shaft is accomplished by a bolt head affixed to the second end of the first central shaft for moving the first plurality of wires from the first configuration to the second configuration in response to a rotation of the bolt head.

17. A method as recited in claim 14 wherein the first central shaft has a threaded first end and a second end fixedly mounted on the first base member, wherein the first compression plate is formed with a hole, and further wherein the step of acting on the first central shaft is accomplished by a nut mounted onto the first end of the first central shaft for moving the first plurality of wires from the first configuration to the second configuration in response to a rotation of the nut.

18. A method as recited in claim 17 wherein the second assembly is a bipartite assembly.

\* \* \* \* \*